United States Patent
Schelberger et al.

(10) Patent No.: US 6,350,765 B1
(45) Date of Patent: Feb. 26, 2002

(54) FUNGICIDAL MIXTURES BASED ON AMIDE COMPOUNDS AND AZOLES

(75) Inventors: Klaus Schelberger, Gönnheim; Maria Scherer, Landau; Karl Eicken, Wachenheim; Manfred Hampel, Neustadt; Eberhard Ammermann, Heppenheim; Gisela Lorenz, Neustadt; Siegfried Strathmann, Limburgerhof, all of (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 0 days.

(21) Appl. No.: 09/581,796
(22) PCT Filed: Dec. 15, 1998
(86) PCT No.: PCT/EP98/08224
  § 371 Date: Jun. 19, 2000
  § 102(e) Date: Jun. 19, 2000
(87) PCT Pub. No.: WO99/31979
  PCT Pub. Date: Jul. 1, 1999

(51) Int. Cl.⁷ .................. A01N 43/40; A01N 43/50; A01N 43/54; A01N 43/64; A01N 55/00
(52) U.S. Cl. .................. 514/355; 514/63; 514/259; 514/383; 514/399
(58) Field of Search .................. 514/355, 383, 514/259, 63, 399

(56) References Cited

U.S. PATENT DOCUMENTS

| | | | |
|---|---|---|---|
| 4,767,774 A | 8/1988 | Bartlett | 514/365 |
| 4,897,407 A | 1/1990 | Bartlett | 514/365 |
| 5,317,027 A | 5/1994 | Sauter | 514/399 |
| 5,399,579 A | 3/1995 | Sauter | 514/383 |
| 5,476,868 A | 12/1995 | Wingert | 514/383 |
| 5,532,260 A | 7/1996 | Wingert | 514/383 |
| 5,587,365 A | 12/1996 | Wingert | 514/63 |

FOREIGN PATENT DOCUMENTS

| | | |
|---|---|---|
| AU | 33173/95 | 5/1996 |
| EP | 0531 837 | 3/1993 |
| EP | 0645 091 | 3/1995 |
| EP | 0707 792 | 4/1996 |
| GB | 2 176 106 | 12/1986 |
| WO | 95/15690 | 6/1995 |
| WO | 97/06678 | 2/1997 |
| WO | 97/08952 | 3/1997 |
| WO | 97/39630 | 10/1997 |

Primary Examiner—Allen J. Robinson
(74) Attorney, Agent, or Firm—Keil & Weinkauf

(57) ABSTRACT

Fungicidal mixtures comprise as active components
a) an amide compound of the formula I $$A-CO-NR^1R^2 \quad\quad I$$

in which
A is an aryl group or an aromatic or non-aromatic, 5- or 6-membered heterocycle which has from 1 to 3 hetero atoms which are selected from O, N and S; where the aryl group or the heterocycle may or may not have 1, 2 or 3 substituents which are selected, independently of one another, from alkyl, halogen, $CHF_2$, $CF_3$, alkoxy, haloalkoxy, alkylthio, alkylsulfinyl and alkylsulfonyl;
$R^1$ is a hydrogen atom;
$R^2$ is a phenyl or cycloalkyl group which may or may not have 1, 2 or 3 substituents which are selected, independently of one another, from alkyl, alkenyl, alkynyl, alkoxy, alkenyloxy, alkynyloxy, cycloalkyl, cycloalkenyl, cycloalkyloxy, cycloalkenyloxy, phenyl and halogen, where the aliphatic and cycloaliphatic radicals may be partially or fully halogenated and/or the cycloaliphatic radicals may be substituted by from 1 to 3 alkyl groups and where the phenyl group may have from 1 to 5 halogen atoms and/or from 1 to 3 substituents which are selected, independently of one another, from alkyl, haloalkyl, alkoxy, haloalkoxy, alkylthio and haloalkylthio, and where the amidic phenyl group may or may not be condensed with a saturated 5-membered ring which may or may not be substituted by one or more alkyl groups and/or may have a hetero atom selected from O and S, and
b) an azole derivative II
in a synergistically effective amount.

16 Claims, No Drawings

FUNGICIDAL MIXTURES BASED ON AMIDE COMPOUNDS AND AZOLES this application is a 371 of PCT/EP98/08224, filed Dec. 15, 1998

The present invention relates to fungicidal mixtures for controlling harmful fungi and also to methods for controlling harmful fungi using such mixtures.

WO 97/08952 describes mixtures of amide compounds of the formula I

A—CO—NR$^1$R$^2$      (I)

in which
- A is an aryl group or an aromatic or non-aromatic, 5- or 6-membered heterocycle which has from 1 to 3 hetero atoms which are selected from O, N and S;
  where the aryl group or the heterocycle may or may not have 1, 2 or 3 substituents which are selected, independently of one another, from alkyl, halogen, CHF$_2$, CF$_3$, alkoxy, haloalkoxy, alkylthio, alkylsulfinyl and alkylsulfonyl;
- R$^1$ is a hydrogen atom;
- R$^2$ is a phenyl or cycloalkyl group which may or may not have 1, 2 or 3 substituents which are selected from alkyl, alkenyl, alkynyl, alkoxy, alkenyloxy, alkynyloxy, cycloalkyl, cycloalkenyl, cycloalkyloxy, cycloalkenyloxy, phenyl and halogen, where the aliphatic and cycloaliphatic radicals may be partially or fully halogenated and/or the cycloaliphatic radicals may be substituted by from 1 to 3 alkyl groups and where the phenyl group may have from 1 to 5 halogen atoms and/or from 1 to 3 substituents which are selected, independently of one another, from alkyl, haloalkyl, alkoxy, haloalkoxy, alkylthio and haloalkylthio, and where the amidic phenyl group may be condensed with a saturated 5-membered ring which may or may not be substituted by one or more alkyl groups and/or may have a hetero atom selected from O and S, and the active ingredient fenazaquin which is known as an acaricide.

These mixtures are described as being particularly effective against Botrytis.

EP-B 531,837, EP-A 645,091 and WO 97/06678 disclose fungicidal mixtures which contain one of the azoles II.1 to II.17 as an active ingredient component.

1-[(2RS,4RS;2RE,4SR)-4-bromo-2-(2,4-dichlorophenyl) tetra-hydrofuryl]-1H-1,2,4-triazole (II.1)

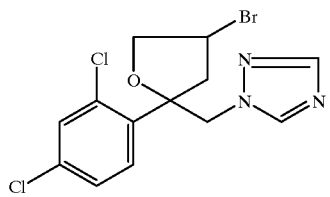

2-(4-chlorophenyl)-3-cyclopropyl-1-(1H-1,2,4-triazol-1-yl)-butan-2-ol (II.2)

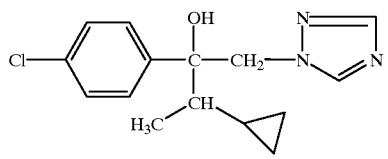

(±)-4-chloro-4-[4-methyl-2-(1H-1,2,4-triazol-1-ylmethyl)-1,3-dioxolan-2-yl]phenyl 4-chlorophenyl ether (II.3)

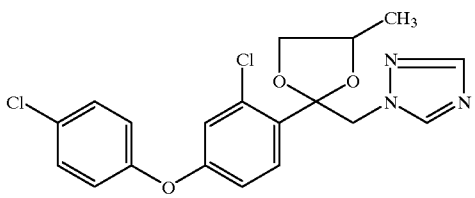

(E)-(R,S)-1-(2,4-dichlorophenyl)-4,4-dimethyl-2-(1H-1,2,4-triazol-1-yl)pent-1-en-3-ol (II.4)

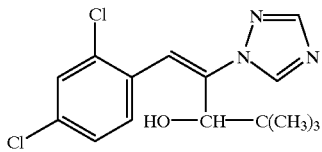

(Z)-2-(1H-1,2,4-triazol-1-ylmethyl)-2-(4-fluorophenyl)-3-(2-chlorophenyl)-oxirane (II.5)

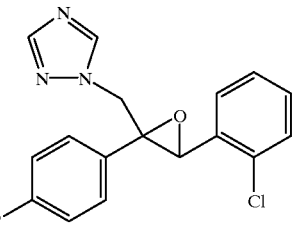

4-(4-chlorophenyl)-2-phenyl-2-(1H-1,2,4-triazolylmethyl)-butyronitrile (II.6)

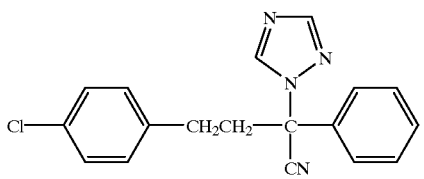

3-(2,4-dichlorophenyl)-6-fluoro-2-(1H-1,2,4-triazol-1-yl)-quinazolin-4(3H)-one (II.7)

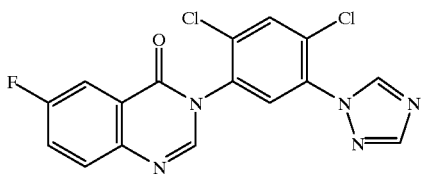

bis(4-fluorophenyl)(methyl)(1H-1,2,4-triazol-1-ylmethyl)-silane (II.8)

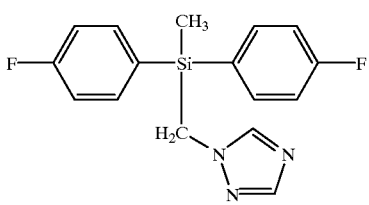

(R,S)-2-(2,4-dichlorophenyl)-1-(1H-1,2,4-triazol-1-yl)-hexan-2-ol (II.9)

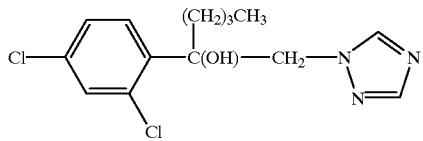

(1RS,5RS;1RS,5SR)-5-(4-chlorobenzyl)-2,2-dimethyl-1-(1H-1,2,4-triazol-1-ylmethyl)cyclopentanol (II.10)

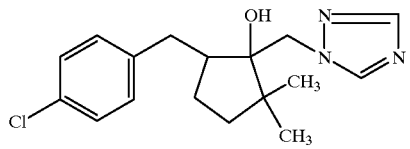

N-propyl-N-[2-(2,4,6-trichlorophenoxy)ethyl]imidazol-1-carboxamide (II.11)

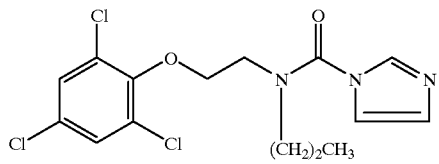

(±)-1-[2-(2,4-dichlorophenyl)-4-propyl-1,3-dioxolan-2-ylmethyl]-1H-1,2,4-triazole (II.12)

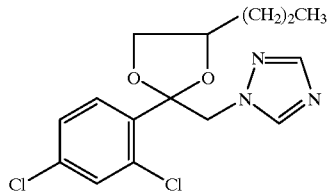

(R,S)-1-(4-chlorophenyl)-4,4-dimethyl-3-(1H-1,2,4-triazol-1-ylmethyl)pentan-3-ol (II.13)

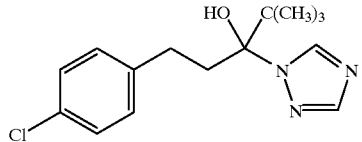

(±)-2-(2,4-dichlorophenyl)-3-(1H-1,2,4-triazolyl)propyl 1,1,2,2-tetrafluoroethyl ether (II.14)

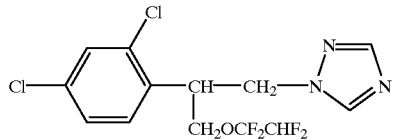

(E)-1-[1-[[4-chloro-2-(trifluoromethyl)phenyl]imino]-2-propoxyethyl ]-1H-imidazole (II.15)

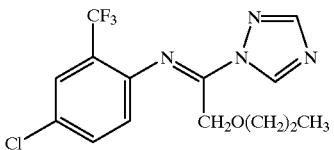

(RS)-2,4'-difluoro-α-(1H-1,2,4-triazol-1-ylmethyl) benzhydryl alcohol (II.16)

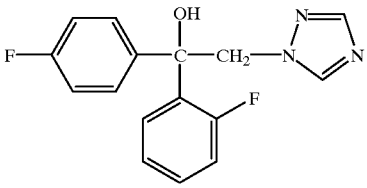

2-p-chlorophenyl-2-(1H-1,2,4-triazol-1-ylmethyl) hexanenitrile (II.17)

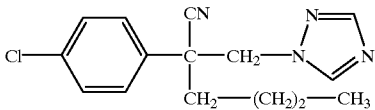

The azole derivatives II, their preparation and their action against harmful fungi is known per se:

II.1: common name: bromuconazol, Proc. Br. Crop Prot. Conf.-Pests Dis., 5-6, 439 (1990);

II.2: common name: cyproconazol, U.S. Pat. No. 4,664,696;

II.3: common name: difenoconazol, GB-A 2,098,607;

II.4: common name: diniconazol, CAS RN [83657-24-3];

II.5: common name (proposed): epoxiconazol, EP-A 196 038;

II.6: common name: fenbuconazol (proposed), EP-A 251 775;

II.7: common name: fluquinconazol, Proc. Br. Crop Prot. Conf.-Pests Dis., 5-3, 411 (1992);

II.8: common name: flusilazol, Proc. Br. Crop Prot. Conf.-Pests Dis., 1, 413 (1984);

II.9: common name: hexaconazol, CAS RN [79983-71-4];

II.10: common name: metconazol, Proc. Br. Crop Prot. Conf.-Pests Dis., 5-4, 419 (1992);

II.11: common name: prochloraz, U.S. Pat. No. 3,991,071;

II.12: common name: propiconazol, GB-A 1,522,657;

II.13: common name: tebuconazol, U.S. Pat. No. 4,723,984;

II.14: common name: tetraconazol, Proc. Br. Crop Prot. Conf.-Pests Dis., 1, 49 (1988);

II.15: common name: triflumizol, JP-A 79/119,462

II.16: common name: flutriafol, CAS RN [76674-21-0]

II.17: common name: myclobutanil, CAS RN [88671-89-0].

It is an object of the present invention to provide other compositions for controlling harmful fungi and in particular for certain indications.

We have found that this object is achieved by a mixture which comprises as active ingredients amide compounds of the formula I defined at the outset and as further fungicidally active component a fungicidal active ingredient from the class of the azoles II.1 to II.17.

The mixtures according to the invention have synergistic action and are therefore particularly suitable for controlling harmful fungi and in particular powdery mildew fungi in vegetables and grapevines.

In the context of the present invention, halogen is fluorine, chlorine, bromine and iodine and is in particular fluorine, chlorine and bromine.

The term "alkyl" includes straight-chain and branched alkyl groups. These are preferably straight-chain or branched $C_1$–$C_{12}$-alkyl and in particular $C_1$–$C_6$-alkyl groups. Examples of alkyl groups are alkyl such as, in particular, methyl, ethyl, propyl, 1-methylethyl, butyl, 1-methylpropyl, 2-methylpropyl, 1,1-dimethylethyl, n-pentyl, 1-methylbutyl, 2-methylbutyl, 3-methylbutyl, 1,2-dimethylpropyl, 1,1-dimethylpropyl, 2,2-dimethylpropyl, 1-ethylpropyl, n-hexyl, 1-methylpentyl, 2-methylpentyl, 3-methylpentyl, 4-methylpentyl, 1,2-dimethylbutyl, 1,3-dimethylbutyl, 2,3-dimethylbutyl, 1,1-dimethylbutyl, 2,2-dimethylbutyl, 3,3-dimethylbutyl, 1,1,2-trimethylpropyl, 1,2,2-trimethylpropyl, 1-ethylbutyl, 2-ethylbutyl, 1-ethyl-2-methylpropyl, n-heptyl, 1-methylhexyl, 1-ethylpentyl, 2-ethylpentyl, 1-propylbutyl, octyl, decyl, dodecyl.

Haloalkyl is an alkyl group as defined above which is partially or fully halogenated by one or more halogen atoms, in particular by fluorine and chlorine. Preferably, there are from 1 to 3 halogen atoms present, and the difluoromethyl or the trifluoromethyl group is particularly preferred.

The above statements for the alkyl group and the haloalkyl group apply in a corresponding manner to the alkyl and haloalkyl groups in alkoxy, haloalkoxy, alkylthio, haloalkylthio, alkylsulfinyl and alkylsulfonyl.

The alkenyl group includes straight-chain and branched alkenyl groups. These are preferably straight-chain or branched $C_3$–$C_{12}$-alkenyl groups and in particular $C_3$–$C_6$-alkenyl groups. Examples of alkenyl groups are 2-propenyl, 2-butenyl, 3-butenyl, 1-methyl-2-propenyl, 2-methyl-2-propenyl, 2-pentenyl, 3-pentenyl, 4-pentenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-2-propenyl, 1-ethyl-2-propenyl, 2-hexenyl, 3-hexenyl, 4-hexenyl, 5-hexenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-2-butenyl, 1,2-dimethyl-3-butenyl, 1,3-dime-thyl-2-butenyl, 1,3-dimethyl-3-butenyl, 2,2-dimethyl-3-butenyl, 2,3-dimethyl-2-butenyl, 2,3-dimethyl-3-butenyl, 1-ethyl-2-butenyl, 1-ethyl-3-butenyl, 2-ethyl-2-butenyl, 2-ethyl-3-butenyl, 1,1,2-trimethyl-2-propenyl, 1-ethyl-1-methyl-2-propenyl and 1-ethyl-2-methyl-2-propenyl, in particular 2-propenyl, 2-butenyl, 3-methyl-2-butenyl and 3-methyl-2-pentenyl.

The alkenyl group may be partially or fully halogenated by one or more halogen atoms, in particular by fluorine and chlorine. The alkenyl group preferably has from 1 to 3 halogen atoms.

The alkynyl group includes straight-chain and branched alkynyl groups. These are preferably straight-chain and branched $C_3$–$C_{12}$-alkynyl groups and in particular $C_3$–$C_6$-alkynyl groups. Examples of alkynyl groups are 2-propynyl, 2-butynyl, 3-butynyl, 1-methyl-2-propynyl, 2-pentynyl, 3-pentynyl, 4-pentynyl, 1-methyl-3-butynyl, 2-methyl-3-butynyl, 1-methyl-2-butynyl, 1,1-dimethyl-2-propynyl, 1-ethyl-2-propynyl, 2-hexynyl, 3-hexynyl, 4-hexynyl, 5-hexynyl, 1-methyl-2-pentynyl, 1-methyl-3-pentynyl, 1-methyl-4-pentynyl, 2-methyl-3-pentynyl, 2-methyl-4-pentynyl, 3-methyl-4-pentynyl, 4-methyl-2-pentynyl, 1,2-dimethyl-2-butynyl, 1,1-dimethyl-3-butynyl, 1,2-dimethyl-3-butynyl, 2,2-dime-thyl-3-butynyl, 1-ethyl-2-butynyl, 1-ethyl-3-butynyl, 2-ethyl-3-butynyl and 1-ethyl-1-methyl-2-propynyl.

The above statements for the alkenyl group and its halogen substituents and for the alkynyl group apply in a corresponding manner to alkenyloxy and alkynyloxy.

The cycloalkyl group is preferably a $C_3$–$C_6$-cycloalkyl group, such as cyclopropyl, cyclobutyl, cyclopentyl or cyclohexyl. If the cycloalkyl group is substituted, it preferably has from 1 to 3 $C_1$–$C_4$-alkyl radicals as substituents.

Cycloalkenyl is preferably a $C_4$–$C_6$-cycloalkenyl group, such as cyclobutenyl, cyclopentenyl or cyclohexenyl. If the cycloalkenyl group is substituted, it preferably has from 1 to 3 $C_1$–$C_4$-alkyl radicals as substituents.

A cycloalkoxy group is preferably a $C_5$–$C_6$-cycloalkoxy group, such as cyclopentyloxy or cyclohexyloxy. If the cycloalkoxy group is substituted, it preferably has from 1 to 3 $C_1$–$C_4$-alkyl radicals as substituents.

The cycloalkenyloxy group is preferably a $C_5$–$C_6$-cycloalkenyloxy group, such as cyclopentyloxy or cyclohexyloxy. If the cycloalkenyloxy group is substituted, it preferably has from 1 to 3 $C_1$–$C_4$-alkyl radicals as substituents.

Aryl is preferably phenyl.

If A is a phenyl group, this may have one, two or three of the abovementioned substituents in any position. These substituents are preferably selected, independently of one another, from alkyl, difluoromethyl, trifluoromethyl and halogen, in particular chlorine, bromine and iodine. Particularly preferably, the phenyl group has a substituent in the 2-position.

If A is a 5-membered heterocycle, it is in particular a furyl, thiazolyl, pyrazolyl, imidazolyl, oxazolyl, thienyl, triazolyl or thiadiazolyl radical or the corresponding dihydro or tetrahydro derivatives thereof. Preference is given to a thiazolyl or pyrazolyl radical.

If A is a 6-membered heterocycle, it is in particular a pyridyl radical or a radical of the formula:

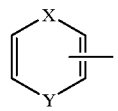

in which one of the radicals X and Y is O, S or $NR^{12}$, where $R^{12}$ is H or alkyl, and the other of the radicals X and Y is $CH_2$, S, SO, $SO_2$ or $NR^9$. The dotted line means that a double bond may or may not be present.

The 6-membered aromatic heterocycle is particularly preferably a pyridyl radical, in particular a 3-pyridyl radical, or a radical of the formula

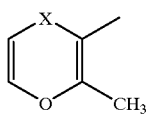
(A3)

in which X is $CH_2$, S, SO or $SO_2$.

The heterocyclic radicals mentioned may or may not have 1, 2 or 3 of the abovementioned substituents, where these substituents are preferably selected, independently of one another, from alkyl, halogen, difluoromethyl or trifluoromethyl.

A is particularly preferably a radical of the formulae:

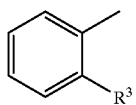
(A1)

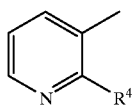
(A2)

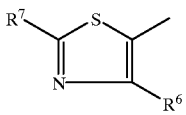
(A5)

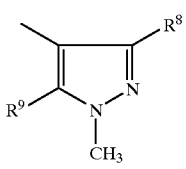
(A7)

in which $R^3$, $R^4$, $R^6$, $R^7$, $R^8$ and $R^9$ independently of one another are hydrogen, alkyl, in particular methyl, halogen, in particular chlorine, $CHF_2$ or $CF_3$.

The radical $R^1$ in the formula I is preferably a hydrogen atom.

The radical $R^2$ in the formula I is preferably a phenyl radical. $R^2$ preferably has at least one substituent which is particularly preferably in the 2-position. The substituent (or the substituents) is (are) preferably selected from the group consisting of alkyl, cycloalkyl, cycloalkenyl, halogen or phenyl.

The substituents of the radical $R^2$ may in turn be substituted again. The aliphatic or cycloaliphatic substituents may be partially or fully halogenated, in particular fluorinated or chlorinated. They preferably have 1, 2 or 3 fluorine or chlorine atoms. If the substituent of the radical $R^2$ is a phenyl group, this phenyl group may preferably be substituted by from 1 to 3 halogen atoms, in particular chlorine atoms, and/or by a radical which is preferably selected from alkyl and alkoxy. Particularly preferably, the phenyl group is substituted with a halogen atom in the p-position, i.e. the particularly preferred substituent of the radical $R^2$ is a p-halogen-substituted phenyl radical. The radical $R^2$ may also be condensed with a saturated 5-membered ring, where this ring for its part may have from 1 to 3 alkyl substituents.

$R^2$ is in this case, for example, indanyl, thiaindanyl and oxaindanyl. Preference is given to indanyl and 2-oxaindanyl which are attached to the nitrogen atom in particular via the 4-position.

According to a preferred embodiment, the composition according to the invention comprises as amide compound a compound of the formula I in which A is as defined below:

phenyl, pyridyl, dihydropyranyl, dihydrooxathiinyl, dihydrooxathiinyl oxide, dihydrooxathiinyl dioxide, furyl, thiazolyl, pyrazolyl or oxazolyl, where these groups may have 1, 2 or 3 substituents which are selected, independently of one another, from alkyl, halogen, difluoromethyl and trifluoromethyl.

According to a further preferred embodiment, A is:

pyridin-3-yl, which may or may not be substituted in the 2-position by halogen, methyl, difluoromethyl, trifluoromethyl, methoxy, methylthio, methylsulfinyl or methylsulfonyl;

phenyl, which may or may not be substituted in the 2-position by methyl, trifluoromethyl, chlorine, bromine or iodine;

2-methyl-5,6-dihydropyran-3-yl;

2-methyl-5,6-dihydro-1,4-oxathiin-3-yl or the 4-oxide or 4,4-dioxide thereof;

2-methylfuran-3-yl, which may or may not be substituted in the 4- and/or 5-position by methyl;

thiazol-5-yl, which may or may not be substituted in the 2- and/or 4-position by methyl, chlorine, difluoromethyl or trifluoromethyl;

thiazol-4-yl, which may or may not be substituted in the 2- and/or 5-position by methyl, chlorine, difluoromethyl or trifluoromethyl;

1-methylpyrazol-4-yl, which may or may not be substituted in the 3- and/or 5-position by methyl, chlorine, difluoromethyl or trifluoromethyl; or oxazol-5-yl, which may or may not be substituted in the 2- and/or 4-position by methyl or chlorine.

According to a further preferred embodiment, the compositions according to the invention comprise as amide compound a compound of the formula I in which $R^2$ is a phenyl group which may or may not be substituted by 1, 2 or 3 of the abovementioned substituents.

According to a further preferred embodiment, the compositions according to the invention comprise as amide compound a compound of the formula I in which $R^2$ is a phenyl group which has one of the following substituents in the 2-position:

$C_3$–$C_6$-alkyl, $C_5$–$C_6$-cycloalkenyl, $C_5$–$C_6$-cycloalkyloxy, cycloalkenyloxy, where these groups may be substituted by 1, 2 or 3 $C_1$–$C_4$-alkyl groups, phenyl which is substituted by from 1 to 5 halogen atoms and/or from 1 to 3 groups which are selected, independently of one another, from $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio and $C_1$–$C_4$-haloalkylthio, indanyl or oxaindanyl which may or may not be substituted by 1, 2 or 3 $C_1$–$C_4$-alkyl groups.

According to a further preferred embodiment, the compositions according to the invention comprise as amide compound a compound of the formula Ia,

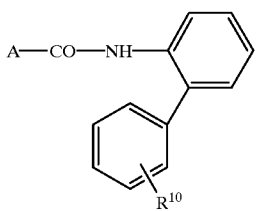

(Ia)

in which
A is

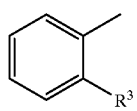
(A1)

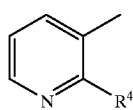
(A2)

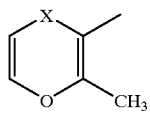
(A3)

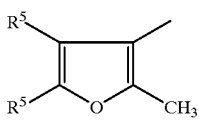
(A4)

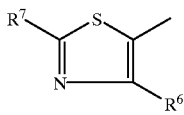
(A5)

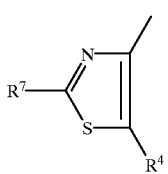
(A6)

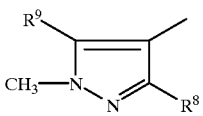
(A7)

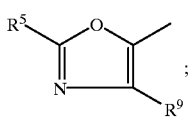
(A8)

X is methylene, sulfur, sulfinyl or sulfonyl ($SO_2$),
$R^3$ is methyl, difluoromethyl, trifluoromethyl, chlorine, bromine or iodine,
$R^4$ is trifluoromethyl or chlorine,
$R^5$ is hydrogen or methyl,
$R^6$ is methyl, difluoromethyl, trifluoromethyl or chlorine,
$R^7$ is hydrogen, methyl or chlorine,
$R^8$ is methyl, difluoromethyl or trifluoromethyl,
$R^9$ is hydrogen, methyl, difluoromethyl, trifluoromethyl or chlorine,
$R^{10}$ is $C_1$–$C_4$-alkyl, $C_1$–$C_4$-alkoxy, $C_1$–$C_4$-alkylthio or halogen.

According to a particularly preferred embodiment, the compositions comprise as amide compound a compound of the formula Ib

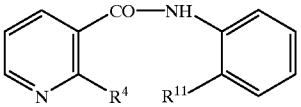

(Ib)

in which
$R^4$ is halogen and
$R^{11}$ is phenyl which is substituted by halogen.

Useful amide compounds of the formula I are mentioned in EP-A-45 545 099 and 589 301 which are incorporated herein in their entirety by reference.

The preparation of the amide compounds of the formula I is known, for example, from EP-A-545 099 or 589 301 or can be carried out by similar processes.

As component II, the mixtures according to the invention comprise an azole derivative II selected from the group of the compounds II.1 to II.17.

To unfold the synergistic action, even a small amount of amide compound of the formula I is sufficient. Amide compound and azole are preferably employed in a weight ratio in the range of from 20:1 to 1:20, in particular from 10:1 to 1:10.

Owing to the basic character of their nitrogen atoms, the azoles II are capable of forming salts or adducts with inorganic or organic acids or with metal ions.

Examples of inorganic acids are hydrohalic acids such as hydrofluoric acid, hydrochloric acid, hydrobromic acid and hydroiodic acid, sulfuric acid, phosphoric acid and nitric acid.

Suitable organic acids are, for example, formic acid and alkanoic acids, such as acetic acid, trifluoroacetic acid, trichloroacetic acid and propionic acid, and also glycolic acid, thiocyanic acid, lactic acid, succinic acid, citric acid, benzoic acid, cinnamic acid, oxalic acid, alkylsulfonic acids (sulfonic acids having straight-chain or branched alkyl radicals of 1 to 20 carbon atoms), arylsulfonic acids or aryldisulfonic acids (aromatic radicals, such as phenyl and naphthyl, which carry one or two sulfo groups), alkylphosphonic acids (phosphonic acids having straight-chain or branched alkyl radicals of 1 to 20 carbon atoms), arylphosphonic acids or aryldiphosphonic acids (aromatic radicals, such as phenyl and naphthyl, which carry one or two phosphonic acid radicals), it being possible for the alkyl or aryl radicals to carry further substituents, e.g. p-toluenesulfonic acid, salicylic acid, p-aminosalicylic acid, 2-phenoxybenzoic acid, 2-acetoxybenzoic acid, etc.

Suitable metal ions are, in particular, the ions of the elements of the first to eighth sub-group, in particular chromium, manganese, iron, cobalt, nickel, copper, zinc and furthermore of the second main group, in particular calcium and magnesium, and of the third and fourth main group, in particular aluminum, tin and lead. The metals can exist in the various valencies which they can assume.

When preparing the mixtures, it is preferred to employ the pure active ingredients I and II, to which further active ingredients against harmful fungi or other pests, such as insects, arachnids or nematodes, or else herbicidal or growth-regulating active ingredients or fertilizers can be admixed.

The mixtures of the compounds I and II, or the compounds I and II used simultaneously, jointly or separately, exhibit outstanding activity against a wide range of phytopathogenic fungi, in particular from the classes of the Ascomycetes, Basidiomycetes, Phycomycetes and Deuteromycetes. Some of them act systemically and can therefore also be employed as foliar- and soil-acting fungicides.

They are especially important for controlling a large number of fungi in a variety of crop plants, such as cotton, vegetable species (e.g. cucumbers, beans, tomatoes, potatoes and cucurbits), barley, grass, oats, bananas, coffee, maize, fruit species, rice, rye, soya, grapevines, wheat, ornamentals, sugar cane, and a variety of seeds.

They are particularly suitable for controlling the following phytopathogenic fungi: *Erysiphe graminis* (powdery mildew) in cereals, *Erysiphe cichoracearum* and *Sphaerotheca fuliginea* in cucurbits, *Podosphaera leucotricha* in apples, *Uncinula necator* in grapevines, Puccinia species in cereals, Rhizoctonia species in cotton, rice and lawns, Ustilago species in cereals and sugar cane, *Venturia inaequalis* (scab) in apples, Helminthosporium species in cereals, Septoria nodorum in wheat, *Botrytis cinerea* (gray mold) in strawberries, vegetables, ornamentals and grapevines, *Cercospora arachidicola* in groundnuts, Pseudocercosporella herpotrichoides in wheat and barley, Pyricularia oryzae in rice, *Phytophthora infestans* in potatoes and tomatoes, Plasmopara viticola in grapevines, Pseudoperonospora species in hops and cucumbers, Alternaria species in vegetables and fruit, Mycosphaerella species in bananas and Fusarium and Verticillium species.

The mixtures according to the invention may particularly preferably be employed for controlling powdery mildew fungi in crops of grapevines and vegetables, and also in ornamentals.

The compounds I and II can be applied simultaneously, that is either together or separately, or in succession, the sequence, in the case of separate application, generally not having any effect on the result of the control measures.

Depending on the kind of effect desired, the application rates of the mixtures according to the invention are, in particular in agricultural crop areas, from 0.01 to 8 kg/ha, preferably 0.1 to 5 kg/ha, in particular 0.5 to 3.0 kg/ha.

The application rates of the compounds I are from 0.01 to 2.5 kg/ha, preferably 0.05 to 2.5 kg/ha, in particular 0.1 to 1.0 kg/ha.

Correspondingly, in the case of the compounds II, the application rates are from 0.01 to 10 kg/ha, preferably 0.05 to 5 kg/ha, in particular 0.05 to 2.0 kg/ha.

For seed treatment, the application rates of the mixture are generally from 0.001 to 250 g/kg of seed, preferably 0.01 to 100 g/kg, in particular 0.01 to 50 g/kg.

If phytopathogenic harmful fungi are to be controlled, the separate or joint application of the compounds I and II or of the mixtures of the compounds I and II is effected by spraying or dusting the seeds, the plants or the soils before or after sowing of the plants, or before or after plant emergence.

The fungicidal synergistic mixtures according to the invention, or the compounds I and II, can be formulated for example in the form of ready-to-spray solutions, powders and suspensions or in the form of highly concentrated aqueous, oily or other suspensions, dispersions, emulsions, oil dispersions, pastes, dusts, materials for broadcasting or granules, and applied by spraying, atomizing, dusting, broadcasting or watering. The use form depends on the intended purpose; in any case, it should ensure as fine and uniform as possible a distribution of the mixture according to the invention.

The formulations are prepared in a known manner, e.g. by extending the active ingredient with solvents and/or carriers, if desired using emulsifiers and dispersants, it being possible also to use other organic solvents as auxiliary solvents if water is used as the diluent. Suitable auxiliaries for this purpose are essentially: solvents such as aromatics (e.g. xylene), chlorinated aromatics (e.g. chlorobenzenes), paraffins (e.g. mineral oil fractions), alcohols (e.g. methanol, butanol), ketones (e.g. cyclohexanone), amines (e.g. ethanolamine, dimethylformamide) and water; carriers such as ground natural minerals (e.g. kaolins, clays, talc, chalk) and ground synthetic minerals (e.g. finely divided silica, silicates); emulsifiers such as nonionic and anionic emulsifiers (e.g. polyoxyethylene fatty alcohol ethers, alkylsulfonates and arylsulfonates) and dispersants such as lignosulfite waste liquors and methylcellulose.

Suitable surfactants are the alkali metal salts, alkaline earth metal salts and ammonium salts of aromatic sulfonic acids, e.g. ligno-, phenol-, naphthalene- and dibutylnaphthalenesulfonic acid, and of fatty acids, alkyl- and alkylarylsulfonates, alkyl, lauryl ether and fatty alcohol sulfates, and salts of sulfated hexa-, hepta- and octadecanols, or of fatty alcohol glycol ethers, condensates of sulfonated naphthalene and its derivatives with formaldehyde, condensates of naphthalene or of the naphthalenesulfonic acids with phenol and formaldehyde, polyoxyethylene octylphenol ether, ethoxylated isooctyl-, octyl- or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene alkyl ethers, lauryl alcohol polyglycol ether acetate, sorbitol esters, lignosulfite waste liquors or methylcellulose.

Powders, materials for broadcasting and dusts can be prepared by mixing or jointly grinding the compounds I or II, or the mixture of the compounds I and II, with a solid carrier.

Granules (e.g. coated granules, impregnated granules or homogeneous granules) are usually prepared by binding the active ingredient, or active ingredients, to a solid carrier.

Fillers or solid carriers are, for example, mineral earths, such as silicas, silica gels, silicates, talc, kaolin, limestone, lime, chalk, bole, loess, clay, dolomite, diatomaceous earth, calcium sulfate, magnesium sulfate, magnesium oxide, ground synthetic materials and fertilizers, such as ammonium sulfate, ammonium phosphate, ammonium nitrate, ureas, and products of vegetable origin, such as cereal meal, tree bark meal, wood meal and nutshell meal, cellulose powders or other solid carriers.

The formulations generally comprise from 0.1 to 95% by weight, preferably 0.5 to 90% by weight, of one of the compounds I or II or of the mixture of the compounds I and II. The active ingredients are employed in a purity of from 90% to 100%, preferably 95% to 100% (according to NMR spectrum or HPLC).

The compounds I or II, the mixtures, or the corresponding formulations, are applied by treating the harmful fungi, their habitat, or the plants, seeds, soils, areas, materials or spaces to be kept free from them with a fungicidally effective amount of the mixture, or of the compounds I and II in the case of separate application.

Application can be effected before or after infection by the harmful fungi.

Examples of such preparations comprising the active ingredients are:

I. A solution of 90 parts by weight of the active ingredients and 10 parts by weight of N-methylpyrrolidone; this solution is suitable for use in the form of microdrops;

II. A mixture of 20 parts by weight of the active ingredients, 80 parts by weight of xylene, 10 parts by weight of the adduct of 8 to 10 mol of ethylene oxide and 1 mol of oleic acid N-monoethanolamide, 5 parts by weight of the calcium salt of dodecylbenzenesulfonic acid, 5 parts by weight of the adduct of 40 mol of ethylene oxide and 1 mol of castor oil; a dispersion is obtained by finely distributing the solution in water;

III. An aqueous dispersion of 20 parts by weight of the active ingredients, 40 parts by weight of cyclohexanone, 30 parts by weight of isobutanol, 20 parts by weight of the adduct of 40 mol of ethylene oxide and 1 mol of castor oil;

IV. An aqueous dispersion of 20 parts by weight of the active ingredients, 25 parts by weight of cyclohexanol, 65 parts by weight of a mineral oil fraction of boiling point 210 to 280° C., and 10 parts by weight of the adduct of 40 mol of ethylene oxide and 1 mol of castor oil;

V. A mixture, ground in a hammer mill, of 80 parts by weight of the active ingredients, 3 parts by weight of the sodium salt of diisobutylnaphthalene-1-sulfonic acid, 10 parts by weight of the sodium salt of a lignosulfonic acid from a sulfite waste liquor and 7 parts by weight of pulverulent silica gel; a spray mixture is obtained by finely distributing the mixture in water;

VI. An intimate mixture of 3 parts by weight of the active ingredients and 97 parts by weight of finely divided kaolin; this dust comprises 3% by weight of active ingredient;

VII. An intimate mixture of 30 parts by weight of the active ingredients, 92 parts by weight of pulverulent silica gel and 8 parts by weight of paraffin oil which had been sprayed onto the surface of this silica gel; this formulation imparts good adhesion to the active ingredient;

VIII. A stable aqueous dispersion of 40 parts by weight of the active ingredients, 10 parts by weight of the sodium salt of a phenolsulfonic acid/urea/formaldehyde condensate, 2 parts by weight of silica gel and 48 parts by weight of water; this dispersion may be diluted further;

IX. A stable oily dispersion of 20 parts by weight of the active ingredients, 2 parts by weight of the calcium salt of dodecylbenzenesulfonic acid, 8 parts by weight of fatty alcohol polyglycol ether, 20 parts by weight of the sodium salt of a phenolsulfonic acid/urea/formaldehyde condensate and 88 parts by weight of a paraffinic mineral oil.

USE EXAMPLE

The synergistic activity of the mixtures according to the invention can be demonstrated by the following experiments:

The active ingredients, separately or together, are formulated as a 10% emulsion in a mixture of 63% by weight of cyclohexanone and 27% by weight of emulsifier, and diluted with water to the desired concentration.

Evaluation is carried out by determining the infected leaf areas in percent. These percentages are converted into efficacies. The efficacy (W) is calculated as follows using Abbot's formula:

$$W = (1-\alpha) \cdot 100/\beta$$

α corresponds to the fungal infection of the treated plants in % and

β corresponds to the fungal infection of the untreated (control) plants in %

An efficacy of 0 means that the infection level of the treated plants corresponds to that of the untreated control plants; an efficacy of 100 means that the treated plants were not infected.

The expected efficacies of the mixtures of the active ingredients were determined using Colby's formula [R. S. Colby, Weeds 15, 20–22 (1967)] and compared with the observed efficacies.

Colby's formula: $E = x + y - x \cdot y/100$

E expected efficacy, expressed in % of the untreated control, when using the mixture of the active ingredients A and B at the concentrations a and b x efficacy, expressed in % of the untreated control, when using active ingredient A at the concentration a y efficacy, expressed in % of the untreated control, when using active ingredient B at the concentration b Activity against Botrytis cinerea on bell peppers Disks of green bell peppers were sprayed to runoff point with an aqueous preparation of active ingredient which had been prepared is from a stock solution comprising 10% of active ingredient, 63% of cyclohexanone and 27% of emulsifier. 2 hours after the spray coating had dried on, the fruit disks were inoculated with a spore suspension of Botrytis cinerea containing $1.7 \times 10^6$ spores per ml of a 2% strength Biomalz solution. The inoculated fruit disks were subsequently incubated in humid chambers at 18° C. for 4 days. The Botrytis infection on the diseased fruit disks was then evaluated visually.

The visually determined values for the percentage of diseased leaf areas were converted into efficacies as percentage of the untreated control. An efficacy of 0 means the same disease level as in the untreated control, an efficacy of 100 means 0% disease. The expected efficacies for active ingredient combinations were determined using Colby's formula (Colby, S. R. "Calculating synergistic and antagonistic responses of herbicide Combinations", Weeds, 15, p. 20–22, 1967) and compared with the observed efficacies.

The compounds of the formula I used were the following components:

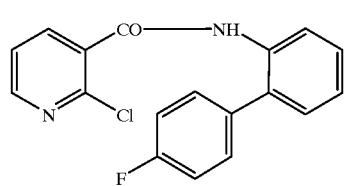

I.1

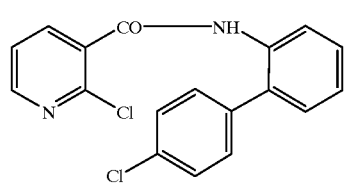

I.2

The results are shown in Tables 1 and 2 below.

TABLE 1

| Ex. | Active ingredient | Concentration of active ingredient in the spray liquor in ppm | Efficacy in % of the untreated control |
|---|---|---|---|
|  | Control (untreated) | 0 (100% disease) | 0 |
| 1C | Compound I.1 | 31 | 60 |
|  |  | 16 | 10 |
| 2C | Compound I.2 | 16 | 80 |
| 3C | Compound II.2 (cyproconazole) | 31 | 10 |
|  |  | 16 | 0 |
| 4C | Compound II.5 (epoxiconazole) | 31 | 0 |
|  |  | 16 | 0 |
| 5C | Compound II.7 (fluquinconazole) | 31 | 0 |
|  |  | 16 | 0 |
| 6C | Compound II.8 (flusilazole) | 31 | 0 |
|  |  | 16 | 0 |
| 7C | Compound II.11 (prochloraz) | 31 | 0 |
|  |  | 16 | 0 |
| 8C | Compound II.12 (propiconazole) | 16 | 0 |
| 9C | Compound II.17 (myclobutanil) | 16 | 0 |

TABLE 2

| Ex. | Mixtures according to the invention (content in ppm) | Observed efficacy | Calculated efficacy* |
|---|---|---|---|
| 10 | 31 ppm I.1 + 31 ppm II.2 | 99 | 64 |
| 11 | 16 ppm I.1 + 16 ppm II.2 | 30 | 10 |
| 12 | 31 ppm I.1 + 31 ppm II.5 | 80 | 60 |
| 13 | 16 ppm I.1 + 16 ppm II.5 | 25 | 10 |
| 14 | 16 ppm I.2 + 16 ppm II.5 | 90 | 80 |
| 15 | 31 ppm I.1 + 31 ppm II.7 | 80 | 60 |
| 16 | 16 ppm I.1 + 16 ppm II.7 | 70 | 10 |
| 17 | 16 ppm I.2 + 16 ppm II.7 | 95 | 80 |
| 18 | 31 ppm I.1 + 31 ppm II.8 | 95 | 60 |
| 19 | 16 ppm I.1 + 16 ppm II.8 | 35 | 10 |
| 20 | 16 ppm I.2 + 16 ppm II.8 | 95 | 80 |
| 21 | 31 ppm I.1 + 31 ppm II.11 | 75 | 60 |
| 22 | 16 ppm I.1 + 16 ppm II.11 | 30 | 10 |
| 23 | 16 ppm I.1 + 16 ppm II.12 | 35 | 10 |
| 24 | 16 ppm I.2 + 16 ppm II.12 | 90 | 80 |
| 25 | 16 ppm I.1 + 16 ppm II.17 | 40 | 10 |
| 26 | 16 ppm I.2 + 16 ppm II.17 | 95 | 80 |

*)calculated using Colby's formula

The experimental results show that, for all mixing ratios, the observed efficacy is higher than the efficacy which had been calculated beforehand using Colby's formula.

What is claimed is:

1. A fungicidal composition comprising synergistically effective amounts of a) an amide compound of formula I $$A-CO-NR^1 R^2 \quad \text{I}$$

in which

A is pyridin-3-yl, which is unsubstituted or substituted in the 2-position by a radical selected from the group of halogen, methyl, difluoromethyl, trifluoromethyl, methoxy, methylthio, methylsulfinyl and methylsulfonyl;

$R^1$ is a hydrogen atom;

$R^2$ is a phenyl group which has one of the following substituents in the 2-position:

$C_3-C_6$-alkyl, $C_5-C_6$-cycloalkenyl, $C_5-C_6$-cycloalkyloxy, $C_5-C_6$-cycloalkenyloxy, where these groups are unsubstituted or substituted by 1, 2 or 3 $C_1-C_4$-alkyl groups, or phenyl which is substituted by from 1 to 5 halogen atoms and/or from 1 to 3 radicals selected from the group consisting of $C_1-C_4$-alkyl, $C_1-C_4$-haloalkyl, $C_1-C_4$-alkoxy, $C_1-C_4$-haloalkoxy, $C_1-C_4$-alkylthio and $C_1-C_4$-haloalkylthio; or is an indanyl group which is unsubstituted or substituted by 1, 2 or 3 $C_1-C_4$-alkyl radicals;

and b) an azole II selected from the group consisting of compounds II.1 to II.17:

1-[(2RS,4RS;2RS,4SR)-4-bromo-2-(2,4-dichlorophenyl)-tetra-hydrofuryl ]-1H-1,2,4-triazole (II.1), 2-(4-chlorophenyl)-3-cyclopropyl-1-(1H-1,2,4-triazol-1-yl)butan-2-ol (II.2), (±)-4-chloro-4-[4-methyl-2-(1-1,2,4-triazol-1-ylmethyl)-1,3-dioxolan-2-yl]phenyl 4-chlorophenyl ether (II.3), (E)-(R,S)-1-(2,4-dichlorophenyl)-4,4-dimethyl-2-(1-1,2,4-triazol-1-yl)pent-1-en-3-ol (II.4), (Z)-2-(1H-1,2,4-triazol-1-ylmethyl)-2-(4-fluorophenyl)-3-(2-chlorophenyl)-oxirane (II.5), 4-(4-chlorophenyl)-2-phenyl-2-(1H-1,2,4-triazolylmethyl)-butyronitrile (II.6), 3-(2,4-dichlorophenyl)-6-fluoro-2-(1H-1,2,4-triazol-1-yl)-quinazolin-4(3H)-one (II.7), bis(4-fluorophenyl)(methyl)(1H-1,2,4-triazol-1-ylmethyl)-silane (II.8), (R,S)-2-(2,4-dichlorophenyl)-1-(1H-1,2,4-triazol-1-yl)-hexan-2-ol (II.9), (1RS,5RS;1RS,5SR)-5-(4-chlorobenzyl)-2,2-dimethyl-1-(1H -1,2,4-triazol-1-ylmethyl) cyclopentanol (II.10), N-propyl-N-[2-(2,4,6-trichlorophenoxy)ethyl] imidazol-1-carboxamide (II.11), (±)-1-[2-(2,4-dichlorophenyl)-4-propyl-1,3-dioxolan-2-yl-methyl]-1H-1,2,4-triazole (II.12), (R,S)-1-(4-chlorophenyl)-4,4-dimethyl-3-(1H-1,2,4-triazol-1-ylmethyl)pentan-3-ol (II.13), (±)-2-(2,4-dichlorophenyl)-3-(1H-1,2,4-triazolyl) propyl 1,1,2,2-tetrafluoroethyl ether (II.14), (E)-1-[1-[[4-chloro-2-(trifluoromethyl)phenyl]imino]-2-propoxyethyl]-1H-imidazole (II.15), (RS)-2,4'-difluoro-α-(1H-1,2,4-triazol-1-ylmethyl) benzhydryl alcohol (II.16) and 2-p-chlorophenyl-2-(1H-1,2,4-triazol-1-ylmethyl) hexanenitrile (II.17).

2. The composition defined in claim 1, wherein the amide compound is a compound of formula Ia

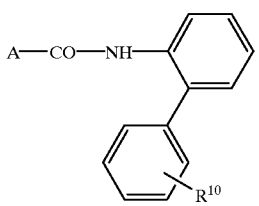

in which

A is a radical of formula A2

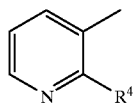

$R^4$ is trifluoromethyl or chlorine, and $R^{10}$ is $C_1$–$C_4$-alkyl, $C_1$–$C_4$-alkoxy, $C_1$–$C_4$-alkylthio or halogen.

3. The composition defined in claim 1, wherein the amide compound is a compound of formula Ib

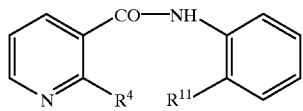

in which $R^4$ is halogen, and $R^{11}$ is phenyl which is substituted by halogen.

4. The composition defined in claim 1, wherein the amide compound is a compound of formula

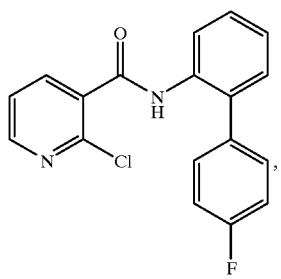

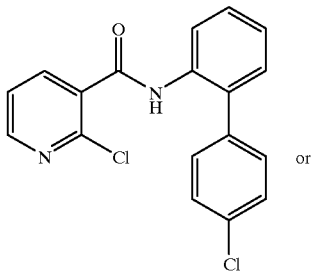

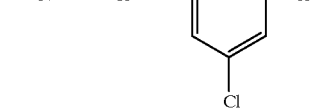

or

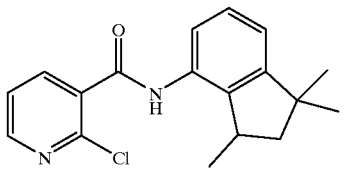

5. The composition defined in claim 1, which is conditioned in two parts, one part comprising the amide compound of formula I in a solid or liquid carrier and the other part comprising the azole II in a solid or liquid carrier.

6. The composition defined in claim 1, wherein the azole II is selected from the group of compounds II.2, II.5, II.7, II.8, II.11, II.12 and II.17.

7. The composition defined in claim 1, which comprises the amide compound of formula I and the azole II in a weight ratio of from 20:1 to 1:20.

8. The composition defined in claim 1, which comprises the amide compound of formula I and the azole II in a weight ratio of from 10:1 to 1:10.

9. A method for controlling harmful fungi, which comprises treating the fungi, their habitat, or materials, plants, seeds, soils, areas or spaces to be protected against fungal attack with an effective amount of the composition defined in claim 1, wherein the amide compound of formula I and the azole II are applied simultaneously together or separately, or in succession.

10. The method of claim 9, wherein the azole II is selected from the group of compounds II.2, II.5, II.7, II.8, II.11, II.12 and II.17.

11. The method of claim 9, wherein the amide compound of formula I and the azole II are applied in a weight ratio of from 20:1 to 1:20.

12. The method of claim 9, wherein the amide compound of formula I and the azole II are applied in a weight ratio of from 10:1 to 1:10.

13. The method of claim 9, wherein the composition is applied in an amount of from 0.01 to 8 kg/ha.

14. The method of claim 9, wherein the composition is applied in an amount of from 0.1 to 5 kg/ha.

15. The method of claim 9, wherein the amide compound of formula I is applied in an amount of from 0.01 to 2.5 kg/ha.

16. The method of claim 9, wherein the azole II is applied in an amount of from 0.01 to 10 kg/ha.

* * * * *

UNITED STATES PATENT AND TRADEMARK OFFICE
CERTIFICATE OF CORRECTION

PATENT NO. : 6,350,765 B1  Page 1 of 1
DATED : February 26, 2002
INVENTOR(S) : Schelberger et al.

It is certified that error appears in the above-identified patent and that said Letters Patent is hereby corrected as shown below:

<u>Title page,</u>
Insert the following priority information:

-- [30] Foreign Application Priority Data
  Dec. 18, 1997 (DE) ......... 197 56 405 --.

<u>Column 16,</u>
Line 32, "(1-1,2,4-triazol-1-" should be -- (1H-1,2,4-triazol-1- --.
Line 35, "-2-(1-1," should be -- -2-(1H-1, --.

Signed and Sealed this

Twentieth Day of August, 2002

Attest:

Attesting Officer

JAMES E. ROGAN
*Director of the United States Patent and Trademark Office*